United States Patent
Sakon et al.

(10) Patent No.: US 12,023,430 B2
(45) Date of Patent: Jul. 2, 2024

(54) VIRUS-COLLECTING FILTER FOR MEDICAL ASPIRATOR SYSTEM

(71) Applicant: GPF Co. Ltd., Tokyo (JP)

(72) Inventors: Yuichi Sakon, Tokyo (JP); Yoshiharu Yabuki, Tokyo (JP); Satoru Kuramoto, Tokyo (JP); Masakazu Masuda, Tokyo (JP)

(73) Assignee: GPF Co. Ltd., Tokyo (JP)

( * ) Notice: Subject to any disclaimer, the term of this patent is extended or adjusted under 35 U.S.C. 154(b) by 902 days.

(21) Appl. No.: 17/043,146

(22) PCT Filed: Dec. 19, 2018

(86) PCT No.: PCT/JP2018/046810
§ 371 (c)(1),
(2) Date: Sep. 29, 2020

(87) PCT Pub. No.: WO2019/187403
PCT Pub. Date: Oct. 3, 2019

(65) Prior Publication Data
US 2021/0252207 A1    Aug. 19, 2021

(30) Foreign Application Priority Data
Dec. 19, 2018  (WO) ............... PCT/JP2018/013896

(51) Int. Cl.
*B01D 39/18*    (2006.01)
*A61M 1/00*    (2006.01)
(Continued)

(52) U.S. Cl.
CPC ............ *A61M 1/60* (2021.05); *A61M 1/604* (2021.05); *B01D 39/12* (2013.01);
(Continued)

(58) Field of Classification Search
CPC ............... A61M 1/60; A61M 1/604; A61M 2205/7509; A61M 2205/7518;
(Continued)

(56) References Cited

U.S. PATENT DOCUMENTS

2014/0296805 A1    10/2014    Arthur et al.

FOREIGN PATENT DOCUMENTS

| JP | H0584280 A | 4/1993 |
| JP | H08216310 A | 8/1996 |

(Continued)

OTHER PUBLICATIONS

Office Action dated Jan. 19, 2023 in corresponding Chinese Patent Application No. 201880092034.4 with partial translation.
(Continued)

*Primary Examiner* — John Kim
(74) *Attorney, Agent, or Firm* — Harness, Dickey & Pierce, P.L.C.

(57) ABSTRACT

Provided is a molded filter used for a flexible disposable bag which is produced so as to be capable of sucking and storing, for example, bodily secretions of a patient and being disposed when a fixed storage amount is reached, wherein a laminate of at least two elements of a powdered hydrophilic swelling agent and a charged nonwoven fabric, and more preferably, a laminate of three elements with a hydrophobic porous film added thereto, is used as a filter base material and the charged nonwoven fabric is arranged downstream of the powdered hydrophilic swelling agent in a direction of flow of expiratory air inside the body. Thus, the molded filter has functions of air permeability that is equal to or higher than a PE sintered body CMC filter, short term and long term waterproof properties, and a better microbial barrier property.

15 Claims, 10 Drawing Sheets

(51) Int. Cl.
*B01D 39/12* (2006.01)
*B01D 39/16* (2006.01)
*B01D 46/00* (2022.01)
*B01D 46/02* (2006.01)
*B01D 46/12* (2022.01)

(52) U.S. Cl.
CPC ......... *B01D 39/1623* (2013.01); *B01D 39/18* (2013.01); *B01D 46/0032* (2013.01); *B01D 46/02* (2013.01); *A61M 2205/7509* (2013.01); *A61M 2205/7518* (2013.01); *B01D 46/12* (2013.01); *B01D 2239/0291* (2013.01); *B01D 2239/0421* (2013.01); *B01D 2239/0428* (2013.01); *B01D 2239/0435* (2013.01); *B01D 2239/0618* (2013.01); *B01D 2239/0622* (2013.01); *B01D 2239/0627* (2013.01); *B01D 2239/065* (2013.01); *B01D 2239/1216* (2013.01); *B01D 2239/1258* (2013.01); *B01D 2279/65* (2013.01)

(58) Field of Classification Search
CPC .... B01D 39/12; B01D 39/1623; B01D 39/18; B01D 46/0032; B01D 46/02; B01D 46/12; B01D 2239/0291; B01D 2239/0421; B01D 2239/0428; B01D 2239/0435; B01D 2239/0618; B01D 2239/0622; B01D 2239/0627; B01D 2239/065; B01D 2239/1216; B01D 2239/1258; B01D 2279/65

See application file for complete search history.

(56) References Cited

FOREIGN PATENT DOCUMENTS

| JP | 2008132405 A | 6/2008 |
| JP | 2010227758 A | 10/2010 |
| JP | 2013220287 A | 10/2013 |
| JP | 2014042538 A | 3/2014 |
| JP | 2015521069 A | 7/2015 |
| JP | 3203434 U | 3/2016 |
| WO | WO-2013177716 A1 | 12/2013 |
| WO | WO-2017188398 A1 | 11/2017 |

OTHER PUBLICATIONS

A member for a vacuum suction drainage bag "High-performance filter and vent", Essentra Porous Technologies, 2014.
"3786-012 Filter Valve", Vacsax Limited Material Specification, Jan. 2012 (in English).
Sen'i Gakkaishi, vol. 51, Issue 5, pp. 206 to 210 (1995).
Sen'i To Kogyo, vol. 49, Issue 2, pp. 56 to 60 (1993).
Kagaku Kogaku Ronbunshu, vol. 18, Issue 2, pp. 240 to 247 (1992).
Morse Mask series catalog, Ace International Japan Inc., Feb. 9, 2009.
International Search Report (in English and Japanese) and Written Opinion (in Japanese) of the International Searching Authority issued in PCT/JP2018/046810, dated Mar. 5, 2019; ISA/JP.

PRIOR ART (A)

AIRFLOW (B)

AIRFLOW

VIRUS-COLLECTING FILTER FOR MEDICAL ASPIRATOR SYSTEM

CROSS REFERENCE TO RELATED APPLICATIONS

This application is a U.S. National Phase Application under 35 U.S.C. 371 of International Application No. PCT/JP2018/046810 filed on Dec. 19, 2018, which is based on and claims the benefit of priority from International PCT Application No. PCT/JP2018/013896 filed Mar. 30, 2018. The entire disclosures of all of the above applications are incorporated herein by reference.

TECHNICAL FIELD

The present invention relates to a disposable bag or container for medical aspirator systems which allows exhaled breath from a patient to be released therethrough, which at the same time sucks in and retains secretions, normal saline, and waste liquids such as blood, and which itself is disposed of after the amount of the secretions and waste liquids retained reaches a certain amount. The present invention also relates to a molded body filter used for the above disposable bag or container, and to a secondary filter to be placed downstream of the bag or container.

BACKGROUND ART

More and more recently-used medical aspirator systems are of a type which includes as their component a flexible bag made of a plastic film or a container that sucks in and retains exhaled breath as well as secretions, normal saline, and waste fluids such as blood (hereinafter referred to as "secretions and the like") from a patient, and is disposed of after the amount of the secretions and the like retained reaches a certain level (herein, an article formed of a film or a sheet is called a bag, and an article formed by injection molding or hollow molding is called a container). The flexible bag or container is thus disposable (and is hereinafter referred to as a disposable bag or the like). Such a disposable bag structurally has to have the following portions: a suction port to guide, into the bag, exhaled breath and secretions and the like sucked in from a patient, and an opening portion to release the air in the bag to a rigid container outside the bag, i.e., an air release port (PATENT LITERATURE 1). The opening portion to release air further needs a filter having air permeability and waterproofness at the same time; the air permeability is for conveying the suction power (negative pressure) from an external suction pump to a suction catheter inserted into the body of a patient, and the waterproofness is for preventing the sucked-in secretions from transuding through the opening portion to the suction pump side (hereinafter, such a filter is referred to as a "primary filter"). Currently, a filter functioning to meet the above two demands is used as an air-permeable, waterproof filter in such a configuration that the air release port is closed by a molded product made of two different materials, that is, a hollow-cylindrical molded product formed by a sintered body of high-molecular-weight polyethylene (PE) immersed in a solution of sodium carboxymethyl cellulose (CMC) and then dried (such an air-permeable, waterproof filter is hereinafter referred to as a "sintered-PE and CMC filter") (PATENT LITERATURE 2).

Usually, the primary filter provided to a disposable bag or the like is the only air-permeable, waterproof filter in one medical aspirator system. However, in some cases, a secondary filter may also be placed at a later stage than the disposable bag or the like to complement the primary filter to prevent accidents where mist of secretions and the like passes through the primary filter and contaminates the suction pump. For example, PATENT LITERATURE 1 discloses an example where an independent filter component (hereinafter referred to as a "secondary filter") is used in a connection hose connecting an aspirator main body and a suction bottle (a rigid container), downstream of the air release portion of a disposable bag. Currently, the only filter usable as this primary filter is the above-described sintered-PE and CMC filter. However, this sintered-PE and CMC filter has major drawbacks as will be described in detail later. In spite of the drawbacks, almost no development and proposal have been made heretofore, including the United States and European countries, as to new filter materials and filters formed using those materials, in comparison to the various prior designs and patents for the shape and placement of the filter.

First, a brief description is given of the basic system of a general-purpose medical aspirator currently used. A basic system 100 is usually structured as schematically shown in FIG. 1:

(1) a disposable bag or the like 110 which is made of a flexible plastic, which includes a suction port 11 to which a suction catheter 18 for sucking in the secretions and the like of a patient or the like is connected and an air release port 13 to, while preventing water leakage, release the air in the bag to the outside of the bag through a filter 12, and which is formed to be able to retain the secretions and the like of the patient or the like within the bag;

(2) a rigid container main body portion 120 and its lid portion 122, the rigid container main body portion 120 housing the disposable bag or the like and having a discharge port 15/suction port 16 for reducing the pressure of the inside of the rigid container main body portion 120;

(3) an aspirator main body 130 which generates suction power by use of an electric motor;

(4) a suction port which conveys the suction power to the catheter 18; and (5) a connection hose 19 which connects the rigid container main body portion 120 and the aspirator main body 130 together and a joint or the like (not shown) used to attach the connection hose 19.

The basic system 100 employs a what-is-called detour air release method. In this method, the disposable bag or the like 110 in (1) is housed in the rigid container main body 120 in (2), and instead of directly connecting the air release port 13 of the bag to the suction port 16 on the aspirator main body 130 side in (3), the discharge port 15 of the rigid container is connected to the suction port 16 on the aspirator side. Then, the pressure inside the rigid container is reduced to thereby release air in the disposable bag or the like through the air release port 13. This method is employed because the bag expands under reduced pressure, which facilitates the retention of the secretions and the like and also removal of the suction bag. There is also a purpose to provide a safety measure to make sure that even if secretions and the like inside the bag accidentally leak through the sintered-PE and CMC filter 12, the secretions and the like may be retained inside the rigid container and not be directly absorbed by the aspiration mechanism on the main body side.

Incidentally, the disposable bag or the like 110 is housed inside the rigid container main body 120, and the suction port 16 on the aspirator main body side is connected to the rigid container discharge port 15. Thus, an air-permeable, waterproof filter for the disposable bag or the like may be attached to the bag in such a manner as to close the air release port from the outside of the bag, or in other words, may be provided to the bag externally. However, in order to house the disposable bag or the like including the air-permeable, waterproof filter inside the rigid container main body 120 as efficiently as possible, it is usually more efficient when the air-permeable, waterproof filter is attached inside the bag. In an example of a disposable bag or the like currently used based on the above-described basic system, a hollow-cylindrical sintered-PE and CMC filter is fitted to a plastic (PP) molded product including a pair of an suction port and an air release port, in such a manner as to close the air release port, and the molded product is housed inside a flexible plastic bag and thermally fused to the plastic bag. Such an internal housing method is thought to be rational in terms of maximization of the capacity of the disposable bag or the like and containment of costs for forming the bag.

The mechanism of sucking secretions from the body of a patient into the disposable bag or the like is as follows. First, the aspirator main body 130 sucks air inside the rigid container through the discharge port 15 of the rigid container main body 120 usually at 20 kPa to 35 kPa, bringing the inside of the rigid container to a reduced pressure state. Thereby, the disposable bag or the like 110 housed in the rigid container expands due to the air pressure difference, and at the same time, the air inside the disposable bag or the like is released through the air release port 13 of the disposable bag or the like 110 via the air-permeable filter attached to the bag. As a result, suction power is generated in the bag 110, causing the secretions and the like of the patient to be sucked into the disposable bag or the like 110 through the suction catheter 18.

PATENT LITERATURE 3 (Published Japanese Translation of PCT International Application No. 2015-521069, "DRAINAGE CONTAINER DEVICE AND SUCTION POUCH UNIT") states in its "PRIOR ART" section that "The suction port (which connects the drainage container device with a suction source and evacuates the suction bag) can be arranged in the lid, and directly connected with the suction bag. It can also be arranged in the rigid drainage container, so that first the drainage container and only then the suction bag situated therein are evacuated." PATENT LITERATURE 3 also suggests that modifications of these forms are mostly within the scope of the known art.

CITATION LIST

Patent Literatures

PATENT LITERATURE 1: Japanese Utility Model Registration No. 3203434
PATENT LITERATURE 2: US 2014/0296805A
PATENT LITERATURE 3: JP-2015-521069A (WO2013/177716)
PATENT LITERATURE 4: WO2017/188398
PATENT LITERATURE 5: JP-2008-132405A
PATENT LITERATURE 6: JP-2013-220287A
PATENT LITERATURE 7: JP-2010-227758A
PATENT LITERATURE 8: JP-2014-042538A
PATENT LITERATURE 9: JP-H05-84280A Non Patent Literatures NON PATENT LITERATURE 1: A member for a vacuum suction drainage bag "High-performance filter and vent", Essentra Porous Technologies, 2014
NON PATENT LITERATURE 2: "3786-012 Filter Valve", Vacsax Limited Material Specification, January 2012
NON PATENT LITERATURE 3: Sen'i Gakkaishi, Volume 51, Issue 5, pp. 206 to 210 (1995)
NON PATENT LITERATURE 4: Sen'i To Kogyo, Volume 49, Issue 2, pp. 56 to 60 (1993)
NON PATENT LITERATURE 5: Kagaku Kogaku Ronbunshu, Volume 18, Issue 2, p. 240 (1992)
NON PATENT LITERATURE 6: Morse Mask series catalog, ACE INTERNATIONAL JAPAN INC.

SUMMARY OF INVENTION

Technical Problem

Regarding a disposable bag or the like, various proposals have been made, mainly in the United States and European countries, as to the forms and arrangement of the suction port and the discharge port and as to the air release method, mainly aiming for easy handling in disposal of the bag and for simplification of the overall structure of the system. However, the most important technical problems to be solved are the fact that the primary filter in the disposable bag or the like is required to have the following three functions. First, the opening portion for air release is required to have air permeability in order for the suction power (negative pressure) from the suction pump to be conveyed to the suction catheter inserted into the body of a patient or the like. Second, the primary filter is required to have waterproofness in order to prevent secretions and the like sucked in through the catheter from transuding from the opening portion to the suction pump side. Third, the primary filter is required to deliver pathogen barrier performance in order to prevent bacteria and viruses contained in the exhaled breath (which are hereinafter collectively referred to as "pathogens") from transuding to the outside of the disposable bag or the like when the air is let out. However, main interests have heretofore been placed on filters efficiently achieving both the air permeability and the waterproofness which are functional elements to make the overall medical aspirator system operate, and the barrier performance against pathogens in released air has been neglected since it is technically extremely difficult to fulfill the above three functions at the same time. For this reason, there has been not much discussion about the barrier performance against pathogens in exhaled breath in particular. However, dispersion of pathogens in the ambient environment is an extremely serious risk which should never be neglected, and the pathogen barrier performance is actually a serious problem the measures for which need to be considered, more seriously than the air permeability and waterproofness functions of the filter.

The disposable bag or the like 110 retains sucked-in secretions and the like in the bag itself and is disposed of after the amount of the retained secretions and the like reaches a predetermined retention amount. It is necessary to prevent the secretions and the like sucked and retained in the bag from leaking from the air release port 13 through the filter portion 12 and contaminating the inside of the rigid container main body 120 and to prevent this from adversely affecting the aspiration mechanism of the aspirator main body 130. Further, in case the secretions and the like leak through the filter portion when air is let out through the discharge port, the filter portion needs to have the pathogen barrier performance as described above. It goes without saying that when exhaled breath is released through the filter or when secretions and the like leak out, it is important whether pathogens contained in them are removed or not. Clearly, the most important problem for the disposable bag or the like in the medical aspirator system is not the shape of the suction port or the air release port or how they are attached, but rather, that the filter (a molded body) placed inside or outside the disposable bag or the like needs to simultaneously satisfy the above-described mutually contradictory three types of performance: air permeability, waterproofness, and pathogen barrier performance.

It is clearly difficult to use a single material to manufacture a filter required to simultaneously satisfy the air permeability, waterproofness, and pathogen barrier performance which are mutually contradictory. This may be the reason why a filter made of only one material has not heretofore been studied or developed much for medical aspirators. Current filters are based on the concept that two materials, namely a polymer molded part and a different polymer swelling material, are combined to make them achieve the air permeability function and the waterproofness function, respectively. Specifically, current air-permeable, waterproof filters are manufactured such that a porous PE-sintered body formed of small PE particles thermally fused and formed into a desired shape is immersed in a water solution of CMC and then dried. The air permeability depends on the porosity of the PE-sintered body, and the standard pore size approximately ranges from 30 μm to 50 μm. In order to have as large a surface area as possible and to reduce the risk of breakage and the like, the PE-sintered body is usually formed into a hollow cylindrical shape which is bottomless on one side and is approximately 3.7 mm to 3.9 mm in thickness. The waterproof function, on the other hand, is exhibited when the CMC, which exists in the form of a coating on the surface of each particle of the PE-sintered body, rapidly swells up upon contact with liquid secretions and the like and closes the pores of the PE-sintered body. For this reason, some American and European companies that manufacture and sell air-permeable, waterproof filters call CMC used for the filters a self-sealing material. Despite the fact that the pore size of the PE-sintered body is large, the bacteria and aerosol removal rates of those filters are described as 99.9% to 99.98% on the pamphlets.

However, a first problem of the current PE-sintered and CMC filters used as standards in Japan and in the world as air-permeable, waterproof filters for medical aspirators is the fundamental lack of long-duration waterproofness. This is due to the high water solubility of CMC that is to deliver the waterproof function. A second problem is the pore size and the pathogen barrier performance of the PE-sintered body. The size of a bacterium ranges from 0.8 μm to 10.0 μm, and that of a virus ranges from 0.02 μm to 1.0 μm. In contrast, as described above, the pore size of the PE-sintered body is much larger than that of a bacterium, let alone a virus. This is a concerning matter.

First, a description is given of the first problem, that is, the high water solubility problem of CMC which is to deliver the waterproof function. When a sintered-PE and CMC filter is immersed in tap water for approximately 24 hours, it is easily observed that a great amount of dissolved CMC has eluted. This explicitly demonstrates that this phenomenon is directly connected to a serious problem where, along with the dissolved CMC, secretions and the like easily leak to the outside through the discharge port of the disposable bag or the like. Below, the waterproof performance required of a disposable bag or the like and the waterproof function exhibited by a current sintered-PE and CMC filter are analyzed and compared in detail.

First, there are two aspects to the waterproofness required of a disposable bag or the like. One aspect relates to long-duration waterproofness. A used disposable bag or the like is incinerated after storage. It is absolutely necessary to prevent that secretions and the like containing bacteria and viruses leak to the outside of the bag during the storage of the bag due to defect in the waterproofness of the bag and cause hygiene problems for the environment, humans, and the like. For example, a risk where a disposable bag or the like gets wet from rain after disposal is easily imaginable. A second aspect relates to instantaneous waterproofness. It is necessary to prevent that when a filter is submerged in secretions and the like during suction, mist or liquid secretions and the like leak through the filter instantaneously and contaminate or adversely affect the inside of the rigid container, and by extension the aspiration mechanism of the aspirator main body, through the air release port 13. As already described, what the sintered-PE and CMC filter is capable of is the second instantaneous waterproof function, and has a serious problem regarding the long-duration waterproofness. Accordingly, current sintered-PE and CMC filters widely used in the world and in Japan lack the long-duration waterproofness.

As the second problem, the problems in the pathogen barrier performance and the pore size of the PE-sintered body are considered. Exhaled breath is sucked into a disposable bag or the like through the suction port along with secretions and the like, and the secretions and the like are retained in the bag, whereas the exhaled breath passes through the air-permeable filter, flows from the rigid container to the aspirator main body, and is ultimately discharged to the outside. Thus, the barrier performance of the air-permeable, waterproof filter against pathogens has to be exhibited for two cases: barrier performance for the exhaled breath; and barrier performance for the secretions and the like leaking through the air-permeable, waterproof filter either alone or along with the CMC solution, as described above. The barrier performance of the filter for the first case, namely the exhaled breath, is generally determined using the indicators based on bacteria and aerosol removal rates (Bacterial Filtration Efficiency test, JIS L1912) and Virus Filtration Efficiency test (conforming to JIS L1912). On the other hand, no established indicators are found for pathogen barrier performance to be delivered when liquid matters leak through the filter. Nonetheless, it is clear that in either case, the size of a pathogen and whether the pore size of the PE-sintered body is small or large are decisively important. Generally, the size of a bacterium is 0.8 μm (*Staphylococcus aureus*) to 10 μm, whereas the pores of a PE-sintered body are approximately 30 μm to 50 μm, although the pore size of the PE-sintered body coated with CMC is unknown. Thus, although claimed to offer high barrier performance based on the bacteria and aerosol removal rate tests, it is presumable that, unless its pores are reduced to 10 μm or below, a PE-sintered body filter essentially does not have a barrier function against bacteria and viruses (pathogens) in terms of barrier performance against liquid matters. Due to the technical restraints of sintering and to the necessity to achieve a certain level of air permeability or higher, it is difficult to reduce the pores of a sintered-PE and CMC filter to 30 μm to 50 μm or smaller. Thus, it has to be said that basically, there are serious concerns about the barrier performance of current sintered-PE and CMC filters against bacteria and viruses (pathogens).

Next, the air permeability of a disposable bag or the like is described. In current medical aspirators, an air-permeable filter in a disposable bag or the like is to have an air permeation flow rate of 20 L/min or more under a suction power (differential pressure) of 60 kPa or higher for a high suction pressure and high flow rate type (JIST7208-1:2012, Electrically powered suction equipment-safety requirements: 59.5) and an air permeation flow rate of 0.5 L to 10 L/min under a suction pressure of 20 kPa or lower for a low suction pressure and low flow rate type (59.7). The air permeation flow rate per unit suction force (1 kPa) and per unit area (1 cm$^2$) is 0.0391 L in NON PATENT LITERATURE 1, which is a current standard PE-sintered waterproof filter, and is 0.0514 L in NON PATENT LITERATURE 2. Thus, in order to obtain a predetermined air permeation rate, NON PATENT LITERATURES 1 and 2 need filter areas of 14.61 cm$^2$ (3.9 cm×3.9 cm) and 11.12 cm$^2$ (3.4 cm×3.4 cm), respectively. The surface areas of NON PATENT LITERATURES 1 and 2, which are hollow-cylindrical, standardized products, are approximately 16 cm$^2$. Presumably, the surface areas of current sintered-PE and CMC filters are thus set to be able to support the high suction pressure and high flow rate type.

As a new technology to improve the three types of performance to be achieved by the above-described sintered-PE and CMC filters at the same time, namely air permeability, waterproofness, and pathogen barrier performance, a technology has recently been disclosed (PATENT LITERATURE 4) which uses a porous polytetrafluoroethylene (PTFE) film and an electrically-charged nonwoven fabric together to simultaneously satisfy required functions, that is, air permeability, both instantaneous and long-duration waterproofness, and pathogen barrier performance. Nonetheless, it is still difficult for such a sintered-PE and CMC filter to replace a current sintered-PE and CMC filter due to such problems as the high-level compatibility of air permeability and waterproofness and economic efficiency.

The present invention aims to provide a filter which solves the problems of long-duration waterproofness fundamentally lacking in a current sintered-PE and CMC filter, has air permeability comparable to that of the current filter, and has barrier performance against bacteria and viruses (pathogens), and to provide, while satisfying economic efficiency, a disposable bag or the like inside or outside of which the filter is to be placed.

Solution to Problem

A filter according to the present invention includes at least three members: a hydrophobic porous film (including a nonwoven fabric which is electrically charged or not electrically charged), a hydrophilic swelling agent such as CMC which swells up upon contact with water and closes a flow passage, and an electrically-charged nonwoven fabric which exhibits barrier performance against pathogens by making use of static electricity. These members are arranged in the order mentioned in the flow direction of sucked-in exhaled breath.

(Achieving Air Permeability and Waterproofness at the Same Time)

As a result of various trial-and-error processes and experiments seeking to develop a new air-permeable, waterproof filter, the inventors have come up with a possibility of achieving a filter that delivers both air permeability performance and waterproof performance by use of a filter base material having powders of a hydrophilic swelling agent such as CMC sandwiched between two hydrophobic porous films such as nonwoven fabrics. To be more specific, the challenge of giving long-duration waterproofness to a hydrophilic swelling agent such as CMC should be overcome by sandwiching the hydrophilic swelling agent such as CMC between hydrophobic porous films in order to reduce flowing and diffusing of water molecules surrounding the swollen hydrophilic swelling agent such as CMC. As for the air permeability, which contradicts the waterproofness, air permeability either equaling or surpassing that of a sintered-PE and CMC filter may be obtained by use of a swelling agent in a solid state, or particularly in a powder state, and by selection of hydrophobic porous films with a certain air permeation rate or higher. Further, since the size of a bacterium ranges approximately from 0.8 µm to 10 µm, controlling the pore size to 1 µm or smaller at maximum should be able to remove a majority of bacteria in theory.

Note that a hydrophilic swelling agent in the present invention refers to one having a property that absorbs water and swells up. As synthetic polymers, polyacrylate-based polymers, polysulfonate-based polymers, maleic anhydride-based polymers, polyacrylamide-based polymers, polyvinyl alcohol-based polymers, polyethylene oxide-based polymers, and the like are known. As naturally-derived polymers, polyglutamic acid-based polymers, polyalginate-based polymers, starch-based polymers, cellulose-based polymers, and the like are known. Specific examples include superabsorbent polymers such as sodium polyacrylate, a graft copolymer of starch and polyacrylate, a saponified copolymer of vinyl acetate and methyl acrylate, a saponified copolymer of vinyl acetate and maleic anhydride, a saponified copolymer of isobutylene and maleic anhydride, and an alkali metal salt of carboxymethyl cellulose. Among others, sodium polyacrylate and sodium carboxymethyl cellulose (CMC) are preferable, and CMC is particularly preferable.

The present invention can achieve air permeability by using a hydrophilic swelling agent in a solid state. Examples of a hydrophilic swelling agent in a solid state include powder of a hydrophilic swelling agent alone, a powder mixture of a hydrophilic swelling agent and powder of an organic substance (such as, e.g., polyethylene or polypropylene microparticles), powder of an inorganic substance (such as, e.g., talc, kaolin, or diatomite), or the like added as a filler, and a sintered body obtained by heating such a mixture. Among others, powder of a hydrophilic swelling agent alone or a sintered body using a mixture of a hydrophilic swelling agent and microparticles of polyethylene or the like is preferable, and it is particularly most preferable to use a hydrophilic swelling agent as is in powder form.

As the hydrophobic porous film such as a nonwoven fabric, as described in NON PATENT LITERATURE 4, a hydrophobic nonwoven fabric with a water resistance of 100 mmAq or higher is preferable, a hydrophobic nonwoven fabric with a water resistance of 400 mmAq or higher is more preferable, and a hydrophobic nonwoven fabric with a water resistance of 900 mmAq or higher is most preferable, the water resistance being according to L1092 of the JIS standards. The material is also important. Polyurethane or polyolefin is preferable, and polyolefins such as polyethylene or polypropylene are most preferable.

(Achieving Air Permeability and Pathogen Barrier Performance at the Same Time)

One of collecting mechanisms of an air filter is the mechanical mechanism, namely, (a) sieving, (b) inertial impaction, (c) interception, and (d) diffusion. Generally, the smaller the pore size, the higher the pathogen barrier performance in accordance with the mechanical mechanism, but the higher the pressure loss. To avoid this drawback, incorporating "electrostatically catching pathogens," which is not a mechanical mechanism but a mechanism of action, allows for attainment of a certain air permeation rate and improvement in the pathogen barrier performance at the same time (NON PATENT LITERATURE 3). As described in PATENT LITERATURE 7, using static electricity, an electrically-charged nonwoven fabric can collect submicron- or nano-sized motes, which are usually hard to remove.

The technique to use both the mechanical mechanism dependent on the pore size and the electrostatic catching is already used for air purifiers having an electrically-charged nonwoven fabric (PATENT LITERATURES 5 to 8). However, as will be described later, it is usually difficult to use an electrically-charged nonwoven fabric (NON PATENT LITERATURE 5) in a filter for a medical disposable bag that deals with a fluid which is a mixture of secretions, normal saline, waste liquids such as blood, and a gas, because the charge amount of the electrically-charged nonwoven fabric is drastically decreased by water and in particular droplets containing an organic substance. A filter base material according to the present invention includes a layer configuration in which powder of a hydrophilic swelling agent such as CMC is sandwiched between two hydrophobic porous films such as nonwoven fabrics described above (such a layer structure is hereinafter referred to as a hydrophobic water-swelling filter) and additionally includes an electrically-charged nonwoven fabric placed with a proper positional relation. The filter base material thus completed simultaneously satisfies three types of performance: air permeability, instantaneous and long-duration waterproofness, and pathogen barrier performance.

(The Configuration of a Laminated Filter)

The filter base material of the present invention formed of a hydrophobic water-swelling filter and an electrically-charged nonwoven fabric may be configured in any manner as long as at least one electrically-charged nonwoven fabric is placed downstream of a hydrophilic swelling substance in the flow direction of sucked-in exhaled breath so that the charge amount of the electrically-charged nonwoven fabric will not decrease by exposure to liquids including sucked secretions. The hydrophobic water-swelling filter and the electrically-charged nonwoven fabric may be used as separate filters or may be molded in one piece, but a one-piece molded body filter is preferable. Also, the electrically-charged nonwoven fabric is what a nonwoven fabric, which is a type of a hydrophobic porous film, is electrically charged. Thus, the filter base material may be configured such that at least the downstream one of the two hydrophobic porous films forming the hydrophobic water-swelling filter is replaced by an electrically-charged nonwoven fabric.

Note that, among air permeability, instantaneous and long-duration waterproofness, and pathogen barrier performance which are the challenges to be overcome by the present invention, the risks due to the lack of the long-duration waterproofness may be reduced to some extent by operational strategies such as specifying a time of disposal and specifying a method of disposal. In such a case, a configuration with two members, namely, a filter in which a hydrophilic swelling substance directly comes into contact with water (hereinafter referred to as a "hydrophilic water-swelling filter) like an existing sintered-PE and CMC filter and an electrically-charged nonwoven fabric is possible. However, it goes without saying that it is necessary even in such a case to place at least one electrically-charged nonwoven fabric at a position downstream of the hydrophilic swelling substance in the flow direction of sucked-in exhaled breath.

For the fabrication of the filter base material, a processing method may be used which sandwiches a hydrophilic swelling agent such as CMC between two or three layers of a hydrophobic porous film and an electrically-charged nonwoven fabric and attaches them together using thermal fusion bonding or an adhesive. Another possible processing method is to sandwich powder of a hydrophilic swelling agent such as CMC between the layers and mechanically integrates them using a fixture. In this method, either a tray-shaped nonwoven fabric with its edge slightly bent upwards from flat or, in the case that the nonwoven fabric is flat, a rubber packing may be used to prevent the hydrophilic swelling agent powder from spilling from the overlap of the plurality of hydrophobic porous films, i.e., an edge portion of the filter, or to prevent water from intruding from such areas to degrade the waterproofness of the filter. The filter surface may be in any shape, but a circle or a polygon such as a square, a rectangle, or a hexagon is preferable in terms of workability and strength, and a circle is most preferable in terms of waterproofness and strength.

Note that PATENT LITERATURE 9 discloses a liquid intrusion prevention apparatus in which a swelling high-molecular substance is sandwiched between porous substances including a nonwoven filter. However, this apparatus merely uses a mechanical pathogen collecting technique which is filtration using porous substances and does not additionally use the electrostatic collecting technique. Thus, the ability to collect minute pathogens such as viruses is insufficient.

To actually use a hydrophobic water-swelling filter as an air-permeable, waterproof filter to be incorporated in a disposable bag or the like for a medical aspirator, experiments were carried out about whether there is a hydrophobic water-swelling filter that solely achieves two discrete demands, namely air permeation rate and waterproofness, and if there is such a filter, how these demands can be achieved at high levels in balance.

Air permeability experiments were carried out using a hydrophobic water-swelling filter in which powder CMC selected as the hydrophilic swelling agent is sandwiched between polypropylene (PP) nonwoven fabrics selected as the hydrophobic porous films. The experiments were carried out assuming that the filter is used in an actual medical disposable bag. The results confirmed that, although there are numerical variations depending on the maximum pore size (air permeation rate) and the area of the hydrophobic porous films, the type of CMC, and how much CMC was added, a sufficient air permeation rate defined in JIST7208-1:2012 "Electrically powered suction equipment-safety requirements" for the high suction pressure and high flow rate type and for the low suction pressure and low flow rate type was obtained with the same area (16 cm$^2$) as an existing sintered-PE and CMC filter.

As for waterproofness, since past studies have shown that the water pressure resistance tests by JIS L1912 are based on the exact same principle as depressurization tests for medical aspirators, water leakage experiments were carried out on a hydrophobic water-swelling filter the air permeation rate of which has been confirmed to be sufficient. The result was very favorable; no water leakage occurred in every case under a suction power (differential pressure) of 85 kPa. In addition, long-duration waterproofness was checked by letting a hydrophobic water-swelling filter which has lost air permeability by coming into contact with water stand all day and night under normal pressure, and no water leakage was detected. The hydrophobic water-swelling filter which has been let stand all day and night was dismantled to evaluate the state of CMC inside. The part that had come into contact with water turned into a gel, but the surrounding part was still in the CMC's initial state, i.e., a powder state. Thus, the effectiveness of the hydrophobic porous film in suppressing flow and diffusion of water molecules was confirmed. It can be determined from these results that the hydrophobic water-swelling filter of the present invention has sufficient waterproofness.

is 4.9 cm$^2$ or greater and the amount of CMC added per unit area is in the range of 0.10 g/cm$^2$ to 0.50 g/cm$^2$, more preferably 0.15 g/cm$^2$ to 0.40 g/cm$^2$, or most preferably 0.20 g/cm$^2$ to 0.30 g/cm$^2$. It has been found that by thus properly selecting a hydrophobic water-swelling filter, it is basically

TABLE 1

| | | Filter specifications | | | CMC | Performance | | Water-proofness |
| | | | | | | Suction | Air | |
| No. | Base material | Thickness (mm) | Shape | Area (cm$^2$) | amount (g/cm$^2$) | Pressure (kPa) | permeability (l/min) | (no water leakage) |
|---|---|---|---|---|---|---|---|---|
| C | Control | — | — | — | — | 35 | 21.0 | — |
| | | | | | | 60 | 23.1 | — |
| | | | | | | 85 | 25.2 | — |
| 1 | PE-sintered body (existing product) | 2.5~~35 | Hollow cylinder | 14.1 | No. DATA | 35 | 16.5 | Good |
| | | | | | | 60 | 19.8 | Good |
| | | | | | | 85 | 22.3 | Good |
| 2 | Hydrophobic water-swelling filter | 1.54 | φ 45 | 15.9 | 0.25 | 35 | 18.9 | Good |
| | | | | | | 60 | 21.2 | Good |
| | | | | | | 85 | 24.1 | Good |
| 3 | Hydrophobic water-swelling filter | 1.54 | φ 35 | 9.6 | 0.25 | 35 | 16.9 | Good |
| | | | | | | 60 | 20.5 | Good |
| | | | | | | 85 | 23.4 | Good |
| 4 | Hydrophobic water-swelling filter | 1.54 | φ 30 | 7.1 | 0.25 | 35 | 16.4 | Good |
| | | | | | | 60 | 39.7 | Good |
| | | | | | | 85 | 22.7 | Good |
| 5 | Hydrophobic water-swelling filter | 1.54 | φ 25 | 4.9 | 0.25 | 35 | 16.0 | Good |
| | | | | | | 60 | 19.2 | Good |
| | | | | | | 85 | 21.5 | Good |
| 6 | Hydrophobic water-swelling filter | 1.54 | φ 45 | 15.9 | 0.00 | 35 | 19.4 | Poor |
| | | | | | | 60 | 22.6 | Poor |
| | | | | | | 85 | 24.2 | Poor |
| 7 | Hydrophobic water-swelling filter | 1.54 | φ 45 | 15.9 | 0.04 | 35 | 19.4 | Fair |
| | | | | | | 60 | 21.9 | Poor |
| | | | | | | 85 | 23.5 | Poor |
| 8 | Hydrophobic water-swelling filter | 1.54 | φ 45 | 15.9 | 0.09 | 35 | 18.9 | Good |
| | | | | | | 60 | 21.4 | Fair |
| | | | | | | 85 | 23.0 | Fair |
| 9 | Hydrophobic water-swelling filter | 1.54 | φ 45 | 15.9 | 0.16 | 35 | 18.7 | Good |
| | | | | | | 60 | 21.2 | Good |
| | | | | | | 85 | 23.0 | Fair |
| 10 | Hydrophobic water-swelling filter | 1.54 | φ 45 | 15.9 | 0.19 | 35 | 18.6 | Good |
| | | | | | | 60 | 21.1 | Good |
| | | | | | | 85 | 22.9 | Fair |
| 11 | Hydrophobic water-swelling filter | 1.54 | φ 45 | 15.9 | 0.31 | 35 | 18.6 | Good |
| | | | | | | 60 | 21.1 | Good |
| | | | | | | 85 | 24.0 | Good |
| 12 | Hydrophobic water-swelling filter | 1.54 | φ 45 | 15.9 | 0.41 | 35 | 18.5 | Good |
| | | | | | | 60 | 21.0 | Good |
| | | | | | | 85 | 23.1 | Good |
| 13 | Hydrophobic water-swelling filter | 1.54 | φ 45 | 15.9 | 0.50 | 35 | 18.3 | Good |
| | | | | | | 60 | 20.8 | Good |
| | | | | | | 85 | 22.8 | Good |

Table 1 summarizes the experiment results of air permeability and waterproofness of hydrophobic water-swelling filters. The results of No. 2 to No. 5 in Table 1 show that an air permeability of 96% or higher, which is comparable to that of the existing PE-sintered body, can be delivered for each suction power even when the filter area is 4.9 cm$^2$. In regard to waterproofness, the results of No. 6 to No. 13 show that it is practically preferable that the amount of CMC added per unit area be in the range of 0.10 g/cm$^2$ to 0.50 g/cm$^2$, more preferably 0.15 g/cm$^2$ to 0.40 g/cm$^2$, or most preferably 0.20 g/cm$^2$ to 0.30 g/cm$^2$.

From these overall results, it has been proved that it is actually possible to obtain a hydrophobic water-swelling filter that simultaneously satisfies the air permeability and the waterproofness required of a disposable bag or the like if the area of the selected hydrophobic water-swelling filter possible to form a filter having air permeability and instantaneous and long-duration waterproofness usable for medical aspirators.

However, forming a molded body filter using a hydrophobic water-swelling filter may further pose the following problems in processing, and countermeasures against those problems need to be found. The problems are (1) how to bond and keep airtightness of the portion where a hydrophobic water-swelling filter 25 is attached to a three-dimensionally shaped component 200 illustrated in FIG. 2A, which is to be the air release flow passage inside the bag, and (2) film tear and airtightness damage which may be caused when the bag is brought to a state of reduced pressure of, e.g., 35 kPa by being sucked by the aspirator main body and the hydrophobic water-swelling filter 25 swells up significantly inside the three-dimensionally shaped component 200.

For the attachment of the hydrophobic water-swelling filter and the three-dimensionally shaped component 200 together, it has been confirmed by experiment that when they are bonded using an adhesive or thermal fusion bonding, the thermally fused portion is sufficiently air-tight under a reduced pressure of 35 kPa. As another method, the areas of the attachment portions along four sides may be increased to attach the hydrophobic water-swelling filter and the three-dimensionally shaped component 200 together with a pressure-sensitive adhesive. Because the hydrophobic water-swelling filter is thin, it is also suitable to use a mechanically integrating method by modifying the three-dimensionally shaped component to have a screwing or fitting mechanism, and pushing the periphery portions of the hydrophobic water-swelling filter from above and below. For an actual thermal fusion bonding method, it is suitable to employ a method where the hydrophobic water-swelling filter is directly laminated on the three-dimensionally shaped component and heated from above with a hot plate.

To prevent the hydrophobic water-swelling filter from swelling up significantly inside the three-dimensionally shaped component, it is effective to place a rib-shaped support portion in an opening portion of the three-dimensionally shaped component at intervals of approximately 10 mm vertically and horizontally, or to use a metallic mesh together with the hydrophobic water-swelling filter. Although FIG. 2A illustrates grid-shaped ribs where vertical ribs and horizontal ribs are orthogonal to each other, the shape of the ribs is not limited to this. The important thing is not to bond the hydrophobic water-swelling filter and the rib portions by thermal fusion bonding so as not to degrade the air permeability performance. It has been actually confirmed that both degradation of air permeability performance and swelling up of the hydrophobic water-swelling filter can be prevented even when the internal pressure of a disposable bag or the like is reduced to, e.g., 35 kPa.

(Filter Having Pathogen Barrier Performance)

As described earlier, if the pore size of the hydrophobic porous film is 1 µm or smaller, a hydrophobic water-swelling filter presumably exhibits bacteria barrier performance and also partially virus barrier performance; however, air permeability is compromised. However, it is decisively important for an air-permeable, waterproof filter to have not only bacteria barrier performance but also virus barrier performance, and in order to establish a medical disposable bag in the truest sense, this hurdle has to be overcome no matter what. To this end, assuming that a hydrophobic water-swelling filter has been technically established, new virus trapping methods other than pore size manipulation were examined.

Dust collecting filters used in pharmaceutical factories and the like are categorized based on their collecting efficiency into general filters, intermediately-sophisticated filters, and super-sophisticated filters. Super-sophisticated filters aim to remove dust particles with a target particle size of 0.3 µm or smaller (HEPA) and of 0.1 m or smaller (ULPA). Nonwoven fabric or glass filter paper is used as a material.

As described earlier, a filter's collecting mechanisms are classified as follows (NON PATENT LITERATURE 3): (a) sieving, (b) inertial impaction, (c) interception, (d) diffusion, and (e) static electricity. The sieving (a) is the pore size of a filter material, and the interception (c) is a phenomenon that occurs when the target particle diameter is 0.1 or greater, and when particles moving with the flow of air come into contact with the surface of a filter material and are collected. The diffusion (d) is collecting of particles with a target particle diameter is 0.5 µm or smaller in association with the Brownian motion of the particles. The static electricity (e) is a mechanism where particles with a target particle size of 0.05 µm to 1.0 µm are collected due to the Coulomb force of static electricity that the filter material has.

The size of a virus is in the range of 0.02 µm (norovirus) to 1.0 µm. The following three approaches are conceivable as a way to allow the above-described hydrophobic water-swelling filter to have pathogen barrier performance:

(1) minimizing the maximum pore size of the hydrophobic water-swelling filter serving as a sieve, (2) applying static electricity to the hydrophobic water-swelling filter to electrically charge the hydrophobic porous film used therein and using its Coulomb force, and (3) additionally using an electrically-charged nonwoven fabric in the hydrophobic water-swelling filter (or laminating an electrically-charged nonwoven fabric on the hydrophobic water-swelling filter) to use its Coulomb force.

If a hydrophobic water-swelling filter is used as an air-permeable, waterproof filter, as detailed in the section from TECHNICAL PROBLEM to SOLUTION TO PROBLEM, it is necessary to satisfy certain levels of air permeability performance and waterproof performance at the same time, and for this reason it is difficult to make the maximum pore size fall in the range of less than 0.2 µm to 1.0 µm. Even if the pore size of 0.2 µm is used, it is not necessarily sufficient from the viewpoint of pathogen barrier performance. Further, the approach to apply static electricity to the hydrophobic water-swelling filter itself poses the following risks. Specifically, application of static electricity causes the hydrophobic water-swelling filter to lose its hydrophobicity and therefore compromises its waterproofness. Also, when the hydrophobic water-swelling filter comes into contact with liquid such as waste liquids from the body, the static electricity applied is attenuated, and the virus collecting function is therefore compromised.

It is presumed that the approach to use an electrically-charged nonwoven fabric with the hydrophobic water-swelling filter (or to integrally laminate an electrically-charged nonwoven fabric on the hydrophobic water-swelling filter) is fully possible in theory, and poses no great difficulty in manufacturing a molded body filter. Thus, detailed examinations were carried out about this approach. By making the hydrophobic water-swelling filter serve as a sieve and using the Coulomb force of the electrically-charged nonwoven fabric, a mechanism combining the mechanical mechanisms (a to d) of the above-described filter's collecting mechanism and the electrostatic absorbing mechanism (e) can be built. The electrostatic Coulomb force alone makes it possible to absorb particles which are 0.05 µm to 1.0 µm, which is comparable to a virus size, and therefore effective barrier performance can be expected against pathogens with a virus size of 1 µm or smaller at the air release portion of a disposable bag. The important condition in this case is to laminate films in such a manner that the nonwoven fabric to which static electricity is applied does not come into contact with liquid such as liquids discharged from the body and that, instead, the hydrophobic water-swelling filter which exhibits waterproofness, comes into contact with liquid such as liquids discharged from the body.

A general method to obtain an electrically-charged nonwoven fabric is by manufacturing a nonwoven fabric from engineering plastics such as a PP resin or a nylon 66 resin, and electrically charging the nonwoven fabric using a corona discharge or a hydrocharging method. Desirably, the charge amount is $2.0\times10^{-10}$ coulombs/cm$^2$ or more in terms of a surface charge density. Further, for the manufacturing method, the meltblown method is desirable since the meltblown method makes it possible to obtain an ultrafine fiber diameter and to manufacture a thin fabric. The spunbond method is also possible. PP meltblown electrically-charged nonwoven fabrics currently produced are ones with a thickness of 0.12 mm to 0.40 mm, a basis weight of 10 g to 40 g/g·m$^2$, and an air permeability of 40 cc/cm$^2$/s for the basis weight of 20 g and 20 cc/cm$^2$/s for the basis weight of 40 g.

To check the effectiveness of such an electrically-charged nonwoven fabric, comparative experiments were carried out on how use of an PP meltblown electrically-charged nonwoven fabric with a hydrophobic water-swelling filter or with an existing sintered-PE and CMC filter changes bacterial filtration efficiency (BFE) and virus filtration efficiency (VFE). Table 2 shows the results.

TABLE 2

| No. | Filter Structure | Filter Component | Thickness (nm) | Amount of CMC added (g/cm$^2$) | BFE (%, average of three outcomes) | VFE (%, average of three outcomes) |
|---|---|---|---|---|---|---|
| 1 Comparative example | Blended | PE-sintered body + CMC | 2.5 | No data | 79.5 | 92.4 |
| 2 Present invention | Laminated | PE-sintered body + CMC Electrically-charged nonwoven fabric | 2.5 0.02 | No data | >99.9 | >99.9 |
| 3 Comparative example | Laminated | PP nonwoven fabric CMC PP nonwoven fabric | 0.77 2.50 0.77 | 4.04 (total) | 0.20 | 94.7 | 95.9 |
| 4 Present invention | Laminated | PP nonwoven fabric CMC PP nonwoven fabric Electrically-charged nonwoven fabric | 0.77 2.50 0.77 0.02 | 4.06 (total) | 0.20 | >99.9 | >99.9 |

As is seen from a comparison between No. 1 and No. 3 in the results in Table 2, better pathogen collecting efficiencies were observed, for both the BFE test and the VFE test, in the filter with CMC sandwiched between PP nonwoven fabrics than in the sintered-PE and CMC filter, but the filter No. 3 is still not at the level of completely shutting out pathogens. By contrast, the filters No. 2 and No. 4 of the present invention which use an electrically-charged nonwoven fabric in addition to the filters No. 1 and No. 3, respectively, exhibited a pathogen collecting efficiency of 99.9% or higher, which is the measurement limit, for both the BFE test and the VFE test. Incidentally, a three-layer electrostatic filter having an electrically-charged nonwoven fabric sandwiched between PP nonwoven fabrics, which is applied to face masks, has been confirmed to reduce the viral infectious titer to 99.9999%, and determined to be capable of removing particles as small as 0.1 µm (NON PATENT LITERATURE 6). The advantage of the filters of the present invention is apparent from this fact as well. Thus, it can be expected that the use of a hydrophobic water-swelling filter or a filter having an electrically-charged nonwoven fabric laminated on a hydrophilic water-swelling filter in a disposable bag or the like of the present invention produces an effect where highly communicable toxic viruses such as the influenza virus or norovirus in particular can be removed with a very high trapping ratio.

Advantageous Effects of Invention

When a molded body filter according to the present invention formed of a hydrophobic water-swelling filter and an electrically-charged nonwoven fabric is used as an air-permeable, waterproof, bacteria and virus (pathogen) barrier filter to be incorporated in a disposable bag or the like, the following advantageous effects are delivered:

(1) The air-permeable, waterproof, and pathogen barrier filter of the present invention delivers perfect waterproofness and can help prevent, for example, a mixture of a CMC solution and secretions and the like from leaking to the outside of the bag, the leaking being feared to occur in disposal or storage of the disposable bag. This leak prevention is fundamentally missing in the existing sintered-PE and CMC filter.

(2) A filter which is a laminate of a hydrophilic water-swelling filter and an electrically-charged nonwoven fabric too exhibits very high pathogen barrier performance, compared to a sintered-PE and CMC filter or a hydrophobic water-swelling filter.

Thus, it can be expected that the air-permeable, waterproof, and pathogen barrier filter of the present invention and particularly the laminated filter of a hydrophobic water-swelling filter and an electrically-charged nonwoven fabric delivers high pathogen barrier performance against not only bacteria but also highly infectious viruses. Also, their high waterproofness prevents leakage of secretions and the like completely. Thus, the present invention can provide a disposable bag or the like which offers higher safety to the environment and people surrounding the patient.

DESCRIPTION OF EMBODIMENTS

A disposable bag or the like having, as its integral part, a molded component which is formed using a hydrophobic CMC electrically-charged filter and the like and which has air permeability and waterproof functions can be manufactured to have various shapes, functions, and sizes. Some representative embodiments of the present invention are given below.

Embodiment 1

Figure 2A:
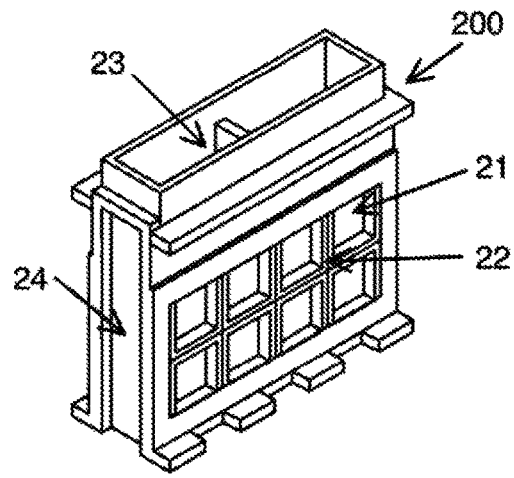
FIG. 2A is a perspective view of a three-dimensionally shaped component used for a disposable bag or the like according to the present invention (before a filter base material is joined).

FIG. 2A is a three-dimensionally shaped component 200 to the opening portion 21 of which a hydrophobic water-swelling filter 25 is to be thermally fused later. This shape is formed by injection molding using a mold and polypropylene (PP) as a raw material. This three-dimensionally shaped component has the opening portion 21, which serves as an area to which the hydrophobic water-swelling filter 25 or the like is to be thermally fused, grid-shaped ribs 22 to support the hydrophobic water-swelling filter 25 in the opening portion, an internal cavity 23 serving as a flow passage for passing air, and a fitting shape 24 for attachment to a molded body illustrated in FIG. 3A. Note that one side, both sides, four side surfaces, or the four side surfaces and the bottom surface of the substantially cuboid molded component may be formed as an opening portion. Also note that the three-dimensionally shaped component 200 may be in various other shapes than a cuboid, such as a hollow cylinder or a discoid. Table 3 shows the area of the opening in a three-dimensionally shaped component which is circular here as a representative example, along with the area of a filter used and that of a packing used.

TABLE 3

| Area of filter | | Area of packing | | Area of opening | |
| --- | --- | --- | --- | --- | --- |
| Shape | mm² | Shape | mm² | Shape | mm² |
| φ55 | 2375 | φ55-φ45 | 785 | φ45 | 1590 |

Figure 2B:
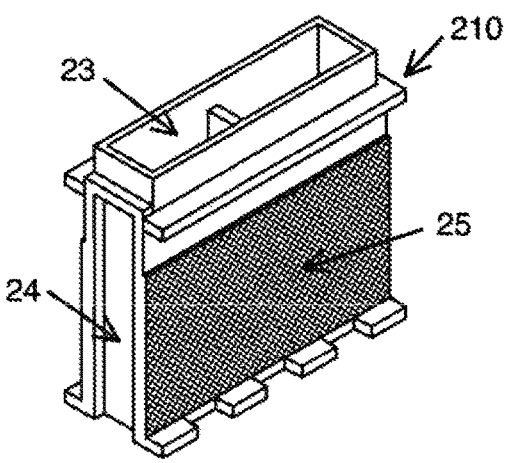
FIG. 2B is a perspective view of a molded body filter (the three-dimensionally shaped component with the filter base material joined thereto) used for a disposable bag or the like according to the present invention.

FIG. 2B illustrates a molded component 210 where a filter base material 25 which is formed of a hydrophobic water-swelling filter or a laminate of a hydrophobic water-swelling film, a PP nonwoven fabric, an electrically-charged nonwoven fabric, and/or the like is thermally fused to the above three-dimensionally shaped component. Hereinbelow, the molded component 210 is called a "molded body filter".

Figure 2C:
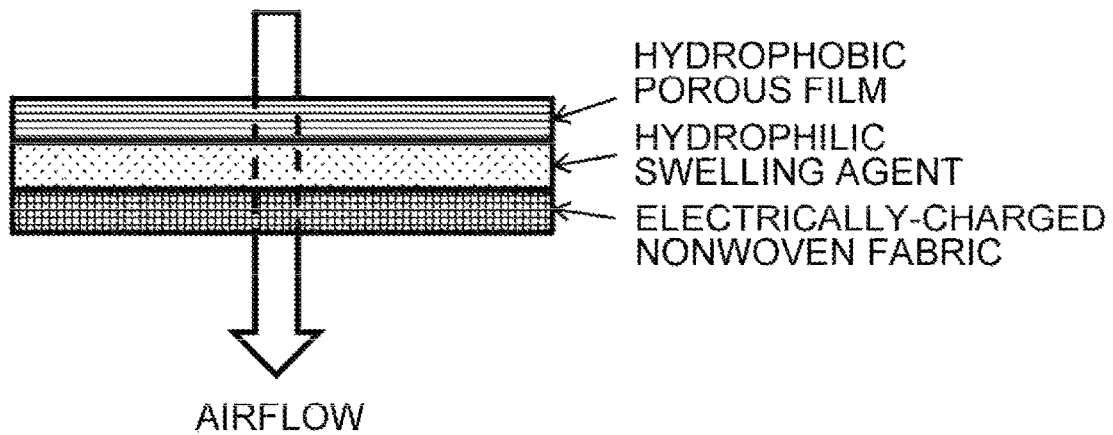
FIG. 2C illustrates an example of a schematic layer configuration of the filter base material which is used for a disposable bag or the like according to the present invention and includes a hydrophobic water-swelling filter, with (A) illustrating an example with three layers and (B) illustrating an example with four layers.
Figure 2C:
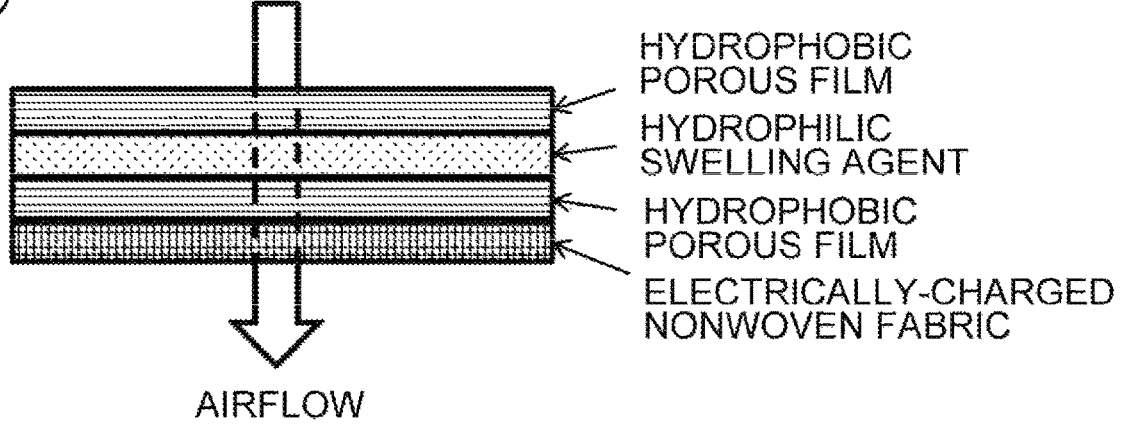

FIG. 2C illustrates an example of the layer structure of the filter base material. The filter base material is configured with at least two layers: (1) a hydrophilic swelling agent in a solid, or particularly powder, state and (2) an electrically-charged nonwoven fabric, but it is more preferable when the filter base material additionally has (3) a hydrophobic porous film and is thus configured with three layers. As preferable configuration examples, part (A) illustrates a case with three layers, and part (B) illustrates a case with four layers. The hydrophobic porous film has to be placed upstream of the hydrophilic swelling agent in the airflow of exhaled breath in order to prevent waste liquids in the film bag from coming into direct contact with the hydrophilic swelling agent. Also, it is more desirable to place the hydrophobic porous film on both sides of the hydrophilic swelling agent in a sandwiching manner. Further, in order to remove not only liquids but also bacteria and viruses, the electrically-charged nonwoven fabric has to be placed downstream of the hydrophilic swelling agent layer in the airflow. As long as these placement conditions are satisfied, additional layers may be placed as needed.

Figure 3A:
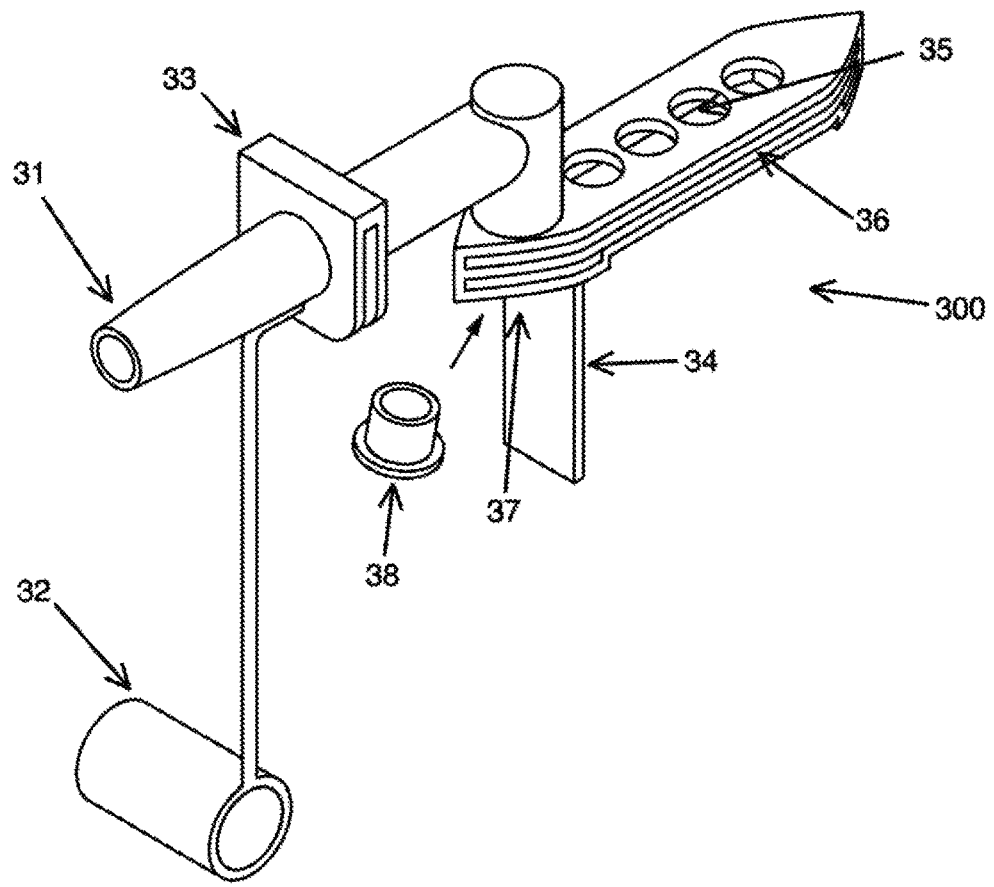
FIG. 3A is a perspective view of an air permeation component used for a disposable bag or the like according to the present invention.

FIG. 3A illustrates the outer appearance of an air permeation component 300 which is manufactured by molding and placed in contact with an inner side of the film bag. The air permeation component 300 includes a suction port 31 to which the suction catheter 18 is to be joined, a cap 32 for the suction port 31, an attachment shape 33 to be attached to the rigid container, a fitting portion 34 to be fitted to the fitting shape 24 of the three-dimensionally shaped component 210, an air release port 35, and a joint portion 36 to be joined with a film bag for retaining secretions and the like by thermal fusion bonding or the like. To prevent secretions and the like retained in a film bag or their mist matters flowing backwards in the suction pipe, a backflow check valve 38 is attached to an outlet 37 of the suction port on the film bag side, the valve 38 being manufactured separately using vulcanized rubber.

Figure 3B:
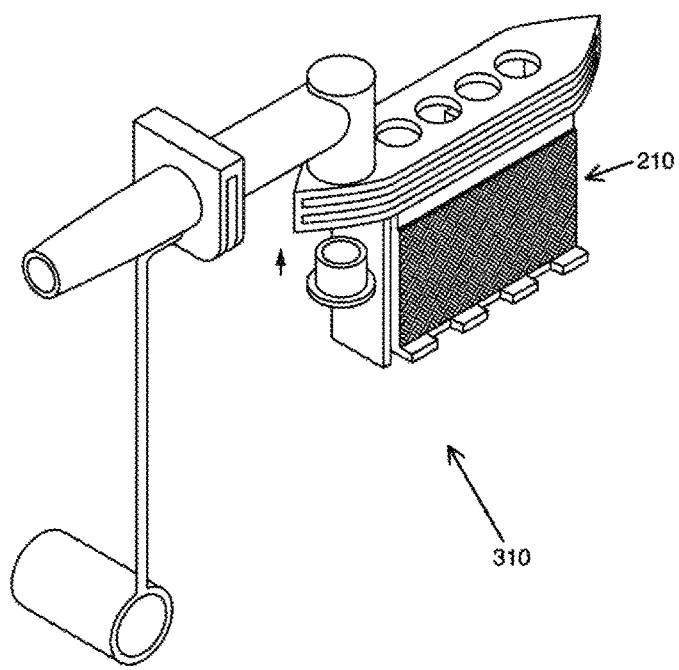
FIG. 3B is a perspective view of the air permeation component used for a disposable bag according to the present invention, with the molded body filter attached thereto.

FIG. 3B illustrates a complex molded body 310 integrally having a molded body filter 210 in FIG. 2B, in which the hydrophobic water-swelling filter is thermally fused, and the air permeation component in FIG. 3A, the molded body filter 210 being fitted to the air permeation component in an airtight manner. Note that this airtight integration can be achieved not only by fitting, but also by thermal fusion bonding of both parts, of course.

Embodiment 2

Figure 3C:
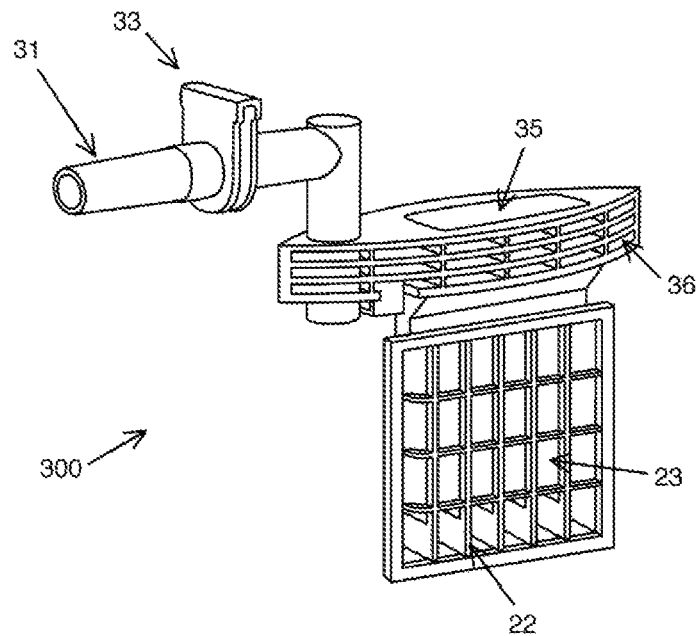
FIG. 3C is a perspective view of the air permeation component used for a disposable bag or the like according to the present invention, the air permeation component being molded in one piece with the three-dimensionally shaped component.
Figure 3D:
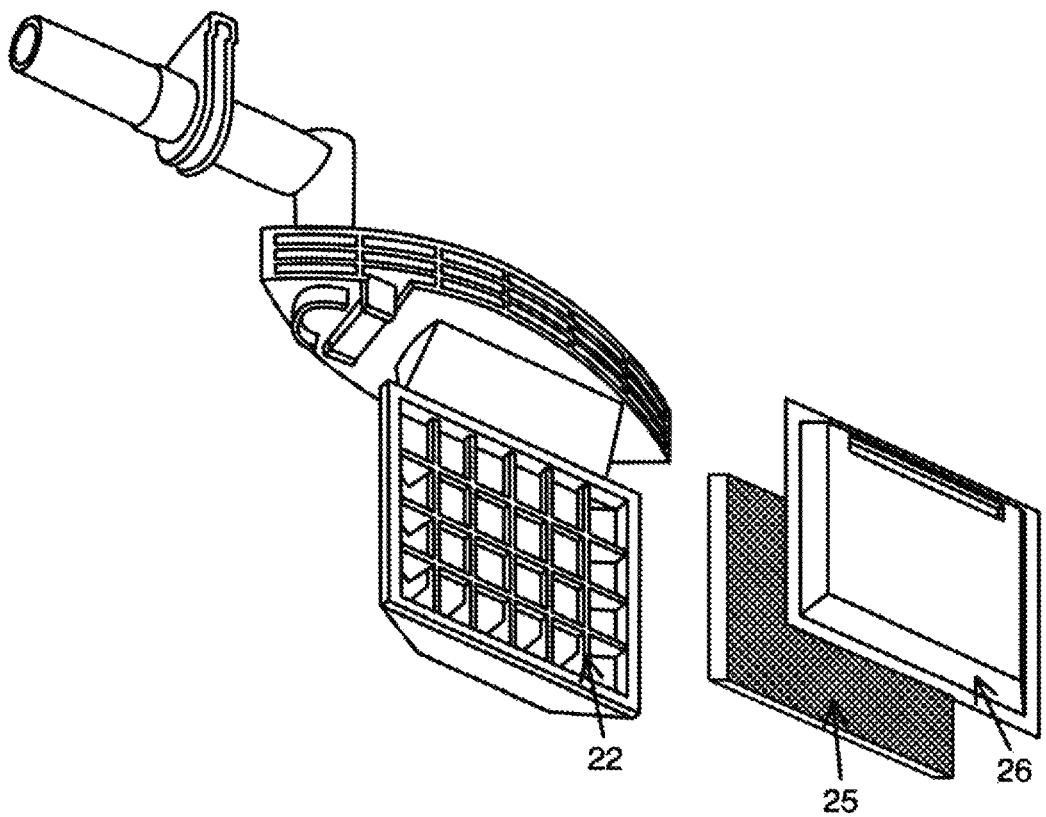
FIG. 3D is a perspective view of the air permeation component of FIG. 3C before the filter base material is joined thereto.
Figure 3E:
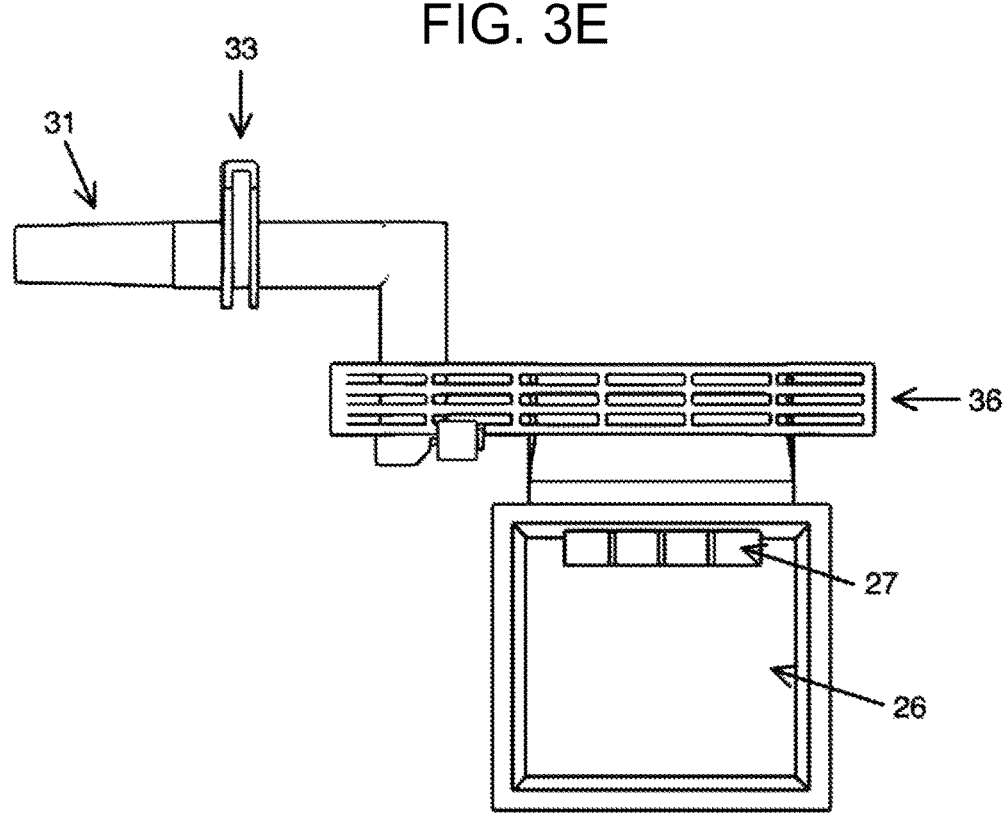
FIG. 3E is a side view of the air permeation component of FIG. 3C after the filter base material is joined thereto.
Figure 3F:
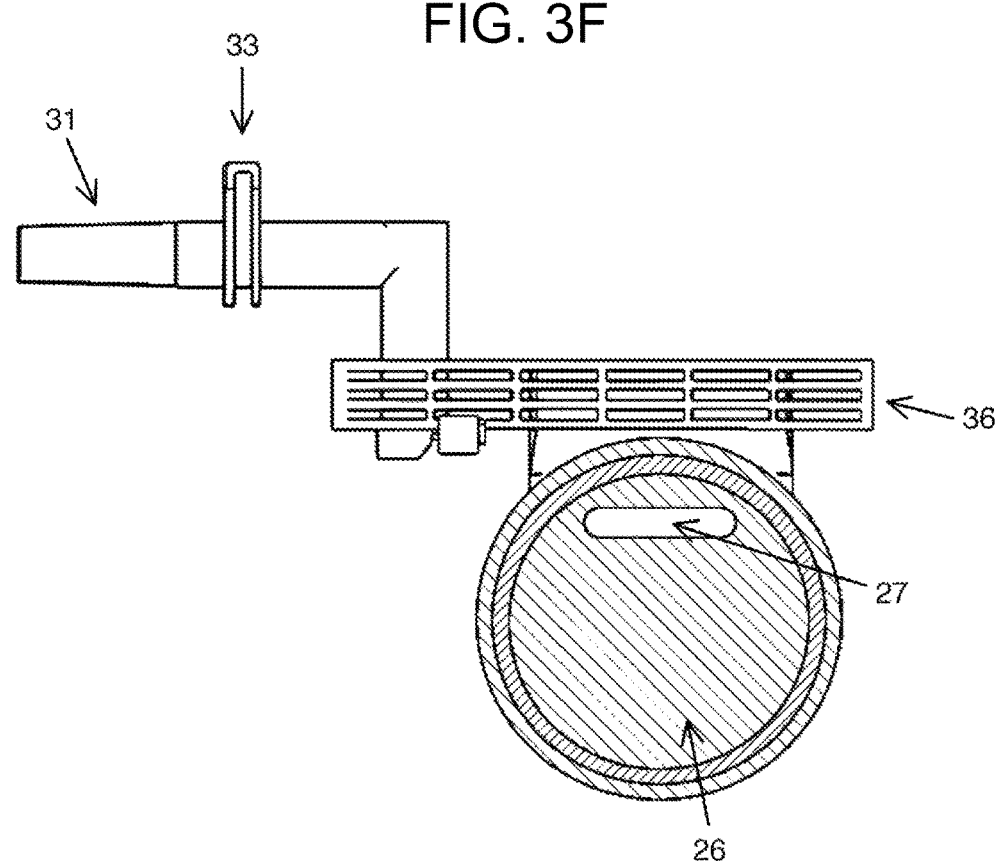
FIG. 3F is a perspective view of the air permeation component which is used for a disposable bag or the like according to the present invention, and to which a circular filter base material is to be joined.
Figure 3G:
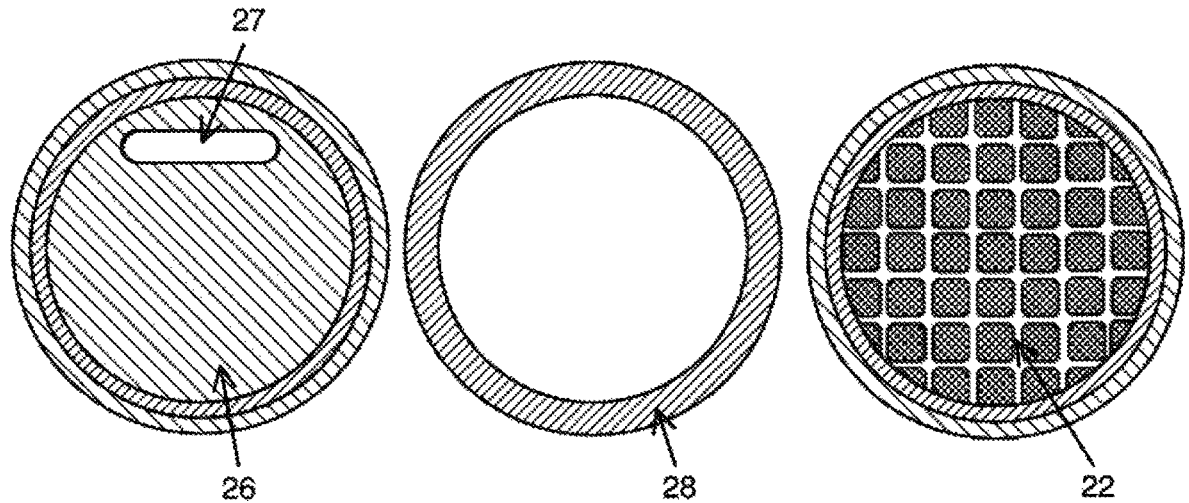
FIG. 3G is an exploded view of a circular three-dimensionally shaped component used for the air permeation component in FIG. 3F, showing a cover, a packing, and ribs from the left.

In FIGS. 3A and 3B, the complex molded body 310 is formed by integration of the molded body filter 210 to the air permeation component 300 in an airtight manner by means of fitting as an example. FIG. 3C illustrates an embodiment where the three-dimensionally shaped component 200 and the air permeation component 300 are molded in one piece. Specifically, the ribs 22 and the internal cavity 23 are formed integrally with the air permeation component 300, and as illustrated in FIG. 3D, the filter base material 25 is sandwiched between the ribs 22 and a cover 26 and is fixed in an airtight manner by thermal fusion bonding, adhesion, or fitting (FIG. 3E). When such cover 26 is used, air can be let in and out of the disposable bag through an air permeation port 27 provided to the cover 26. The air permeation port 27 is provided to an upper portion of the cover 26 so that even if the amount of waste liquids in the disposable bag increases, it will take as much time as possible for the waste liquids to come into contact with the hydrophobic water-swelling filter 25. FIG. 3F illustrates a case where the three-dimensionally shaped component 200 is circular. FIG. 3G illustrates an exploded view of the circular three-dimensionally shaped component 200. The hydrophobic water-swelling filter 25 (not shown) is fixed between the ribs 22 and the cover 26. Also, a packing 28 is placed around the hydrophobic water-swelling filter 25 to prevent waste liquids from leaking from the edge of the filter.

Figure 3H:
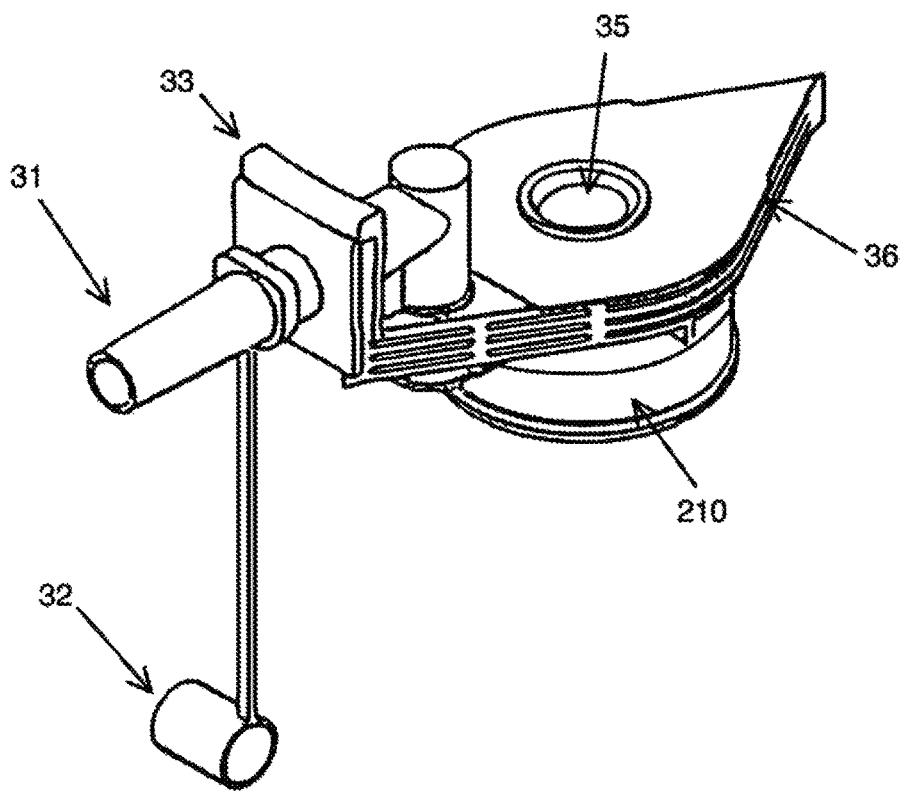
FIG. 3H is a perspective view of an air permeation component used for a disposable bag or the like according to the present invention, the air permeation component having a circular molded body filter attached thereto horizontally with respect to the air permeation component (in the width direction of a flexible bag).

Although the above embodiment illustrates a configuration where the molded body filter 210 is placed vertically, the molded body filter 210 may be attached to a lower portion of the joint portion 36 horizontally as illustrated in FIG. 3H. A film bag 400 is set in such a manner as to house this circular molded body filter, is fused at the joint portion 36, and is thus fixed in an airtight manner. The lower surface of the molded body filter 210 communicates with the inside of the film bag, and the upper surface thereof communicates with the air release port 35.

Figure 4A:
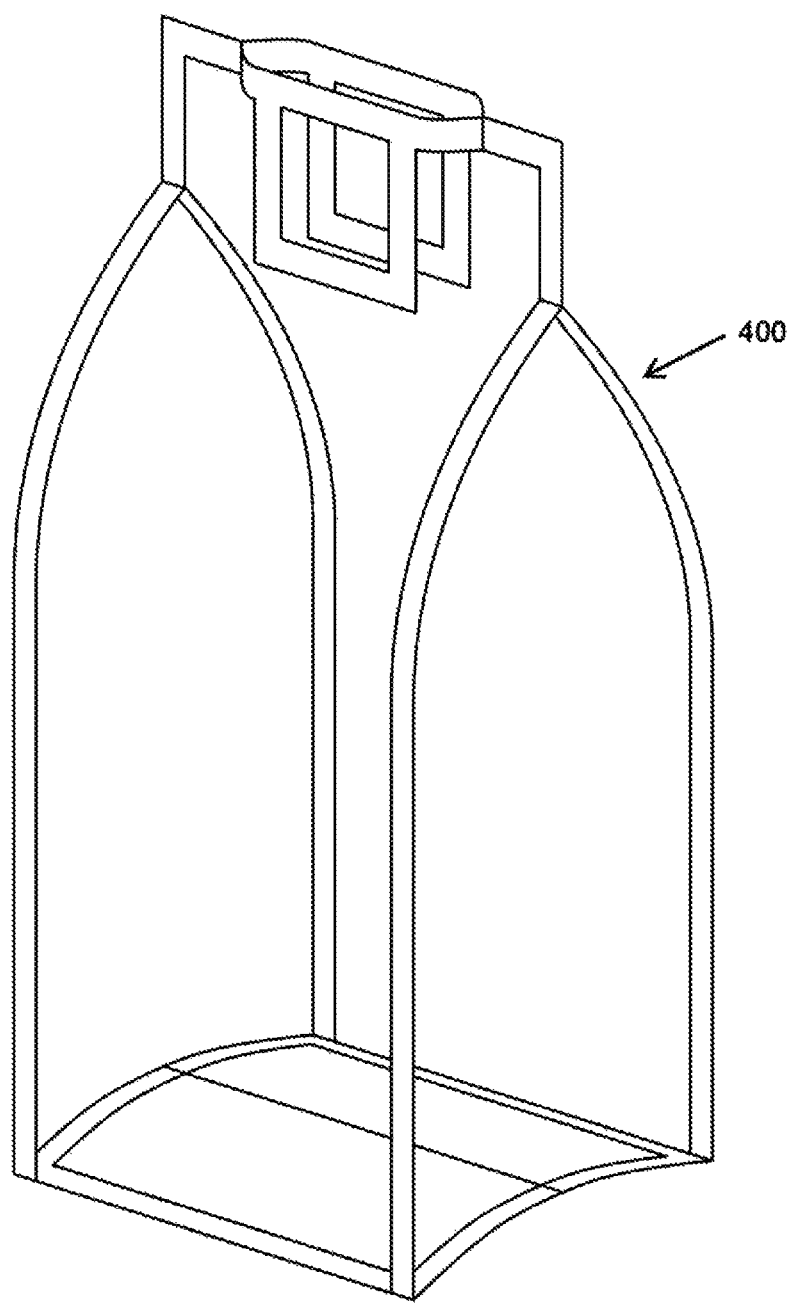
FIG. 4A is a perspective view of a flexible bag used for the disposable bag or the like according to the present invention.

FIG. 4A illustrates an example of a film bag for retaining secretions and the like. Various shapes are possible for the film bag, but it is necessary that the final, integrally-formed disposable bag can be efficiently stored in the rigid container illustrated in FIGS. 5A and 5B. Generally, the film bag is formed by multi-layer inflation molding using linear polyethylene (LLDPE), a polyethylene terephthalate (PET) resin, and/or a nylon resin (NY), and additionally an adhesive resin. In the embodiments of the present invention, the film back includes three layers, with an outer layer (PET) being 30 μm thick, an adhesive resin layer being 7 μm thick, and an inner layer (LLDPE) being 120 μm thick. In this embodiment, the internal volume is 1300 cc.

Figure 4B:
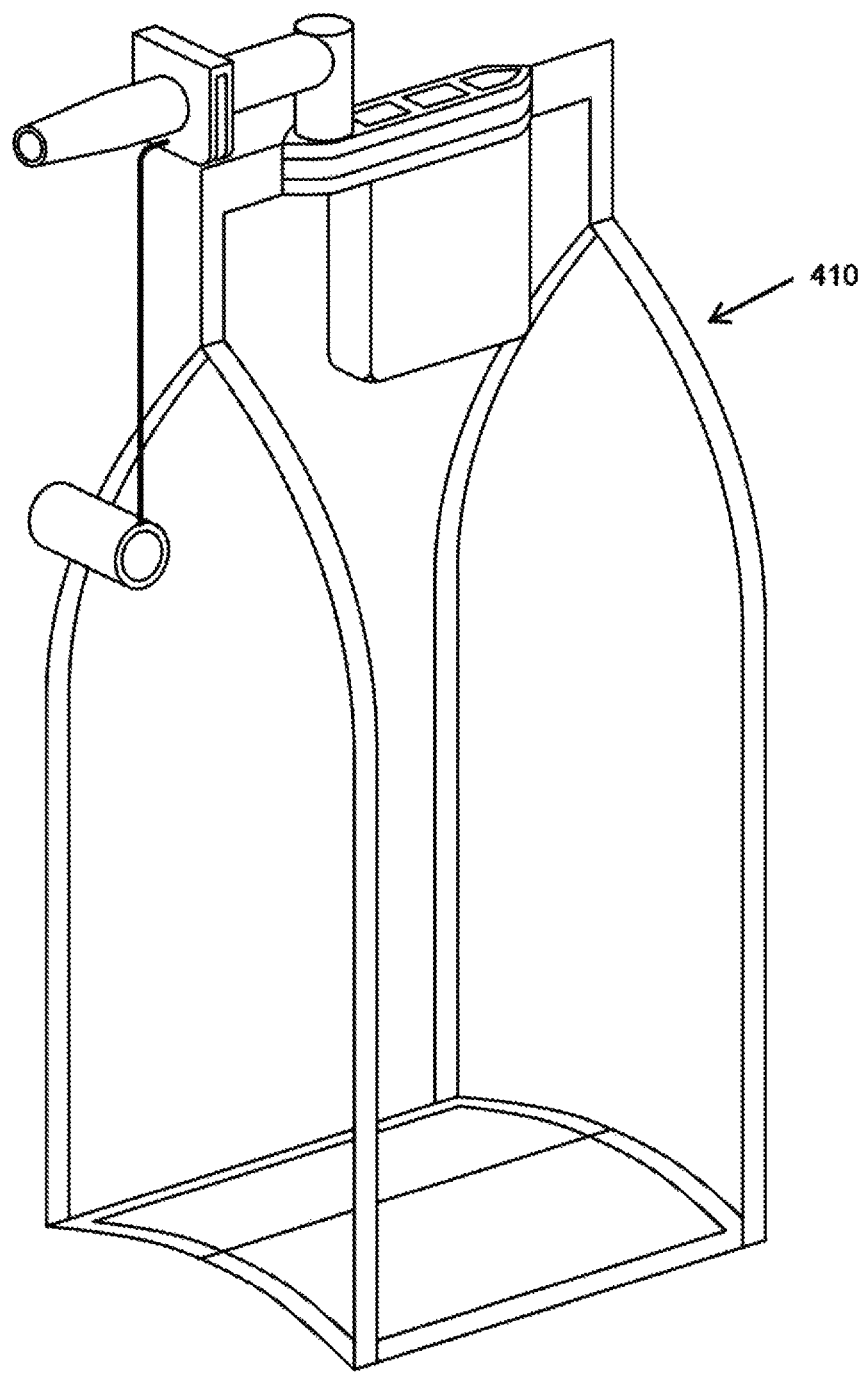
FIG. 4B is a perspective view of the disposable bag or the like according to the present invention after the air permeation component, the three-dimensionally shaped component, and the flexible bag are all joined together.

FIG. 4B illustrates a mode where the complex molded body 310 of FIG. 3B is placed in contact with and thermally fused to the upper, inner edge of the film bag of FIG. 4A in an airtight manner. Thus completed is a final disposable bag 410 for medical aspirators which is formed of the film bag 400 and the integrated complex molded body 310 including the three-dimensionally shaped component 210 which is formed using the hydrophobic water-swelling filter and has air permeability and waterproof functions. This embodiment illustrates an example where the complex molded body 310 is placed in contact with an inner side of the bag, but instead, the complex molded body 310 may be placed in contact with an outer side of the film bag and joined. Additionally, the position at which the complex molded body 310 is attached to the film bag does not have to be the upper edge portion of the film bag 400, but instead, may be at middle positions or higher on the four side surfaces or the corner portions of the side surfaces of the bag.

Embodiment 3

Figure 3I:
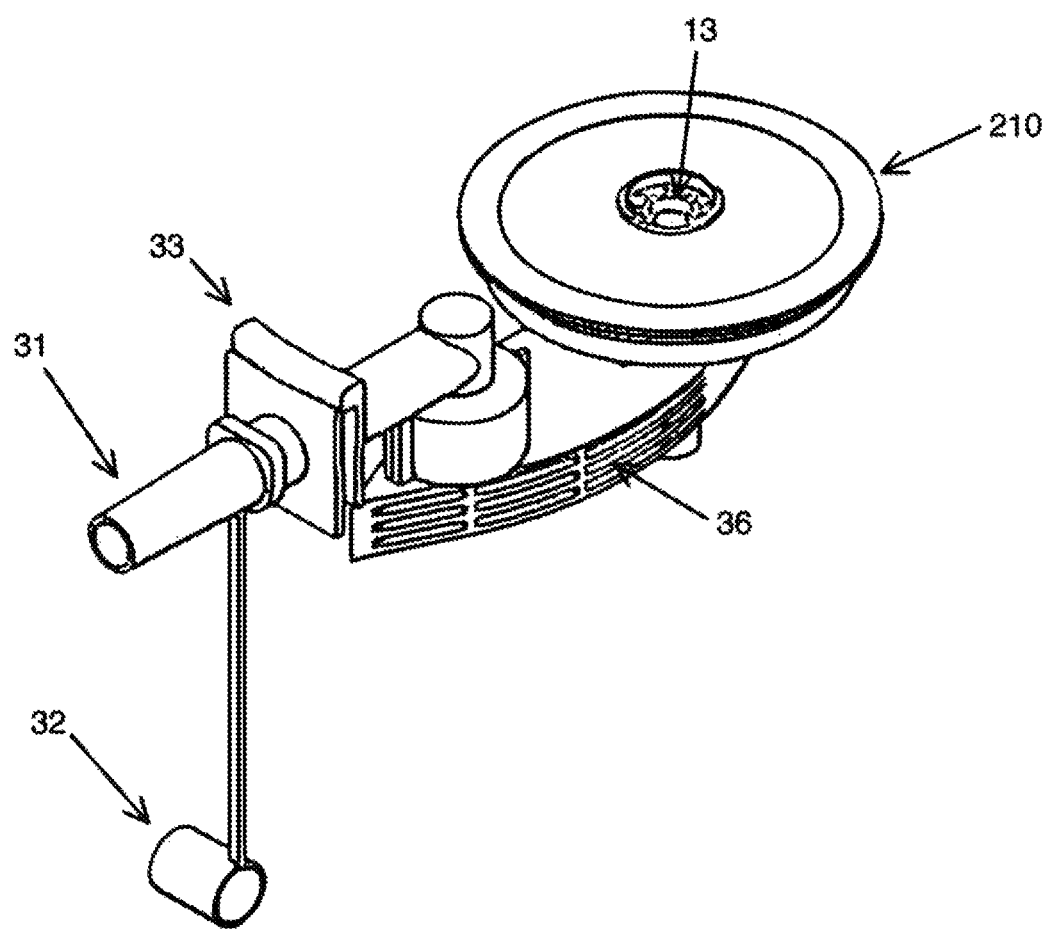
FIG. 3I is a perspective view of the air permeation component used for the disposable bag or the like according to the present invention, the air permeation component having a circular molded body filter attached to an upper portion of the air permeation component (outside of the flexible bag).

To use a detour air release system in which the aspirator main body reduces the pressure in the rigid container and thereby reduces the pressure inside the disposable bag or the like through the air permeation component, Embodiments 1 and 2 described above describe a configuration in which the three-dimensionally shaped component to which the hydrophobic water-swelling filter is thermally fused, that is, the molded body filter is placed inside the disposable bag or the like. To be used for a similar detour air release system, a different configuration may be employed in which the molded body filter is attached to the outside of the disposable bag or the like (i.e., to an upper portion of the air permeation component). FIG. 3I illustrates such an embodiment. In the structure of this embodiment, the circular molded body filter 210 is fixed horizontally to the outer side of the air release port 35, and the airflow goes from the lower side (the inside of the disposable bag or the like) to the air release port 13 on the upper side. Alternatively, a configuration may be employed in which the aspirator main body directly sucks and reduces the pressure in the disposable bag or the like. Using the example of FIG. 3I, a structure may be employed in which the molded body filter 210 is attached to the outer side of the air release port 35 of the air permeation component in an airtight manner, and the connection hose directly connected to the aspirator main body is connected to the outlet side of the molded body filter. By the connection hose (not shown), the air release port 13 is connected to the discharge port 15 provided to a side surface of the rigid container 120, and is thus directly connected to the aspirator main body.

Embodiment 4

As another embodiment, a configuration may be employed in which the molded body filter is provided in contact with the inner side of the discharge port 15 in the rigid container or the lid thereof, and the air release port 35 of the air permeation component 300 is connected to the inlet of the molded body filter with a suction tube, to suck from the suction port 16. Alternatively, the molded body filter may be provided at some midpoint in this suction tube.

Embodiment 5

Figure 1:
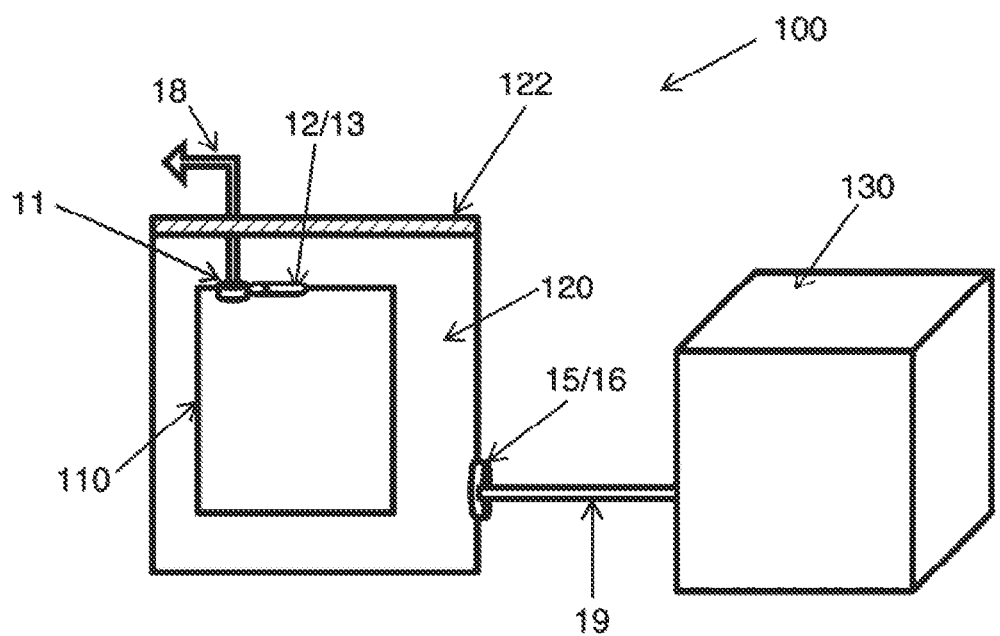
FIG. 1 is a view of the schematic configuration of an existing medical aspirator's basic system.

Embodiments 1 to 4 described above discuss a filter (primary filter) attached to the disposable bag or container into which secretions are sucked or to the inside of the rigid container. As yet another embodiment, a molded body filter according to the present invention including a laminated filter formed of a hydrophilic water-swelling filter and an electrically-charged nonwoven fabric or of a hydrophobic water-swelling filter and an electrically-charged nonwoven fabric may be used as a secondary filter to be connected downstream of the rigid container. In other words, the molded body filter may be connected to the connection hose 19, which connects the rigid container 120 and the aspirator main body 130 in FIG. 1, in an airtight manner to shield outside air. This allows even higher pathogen barrier performance.

Figure 5A:
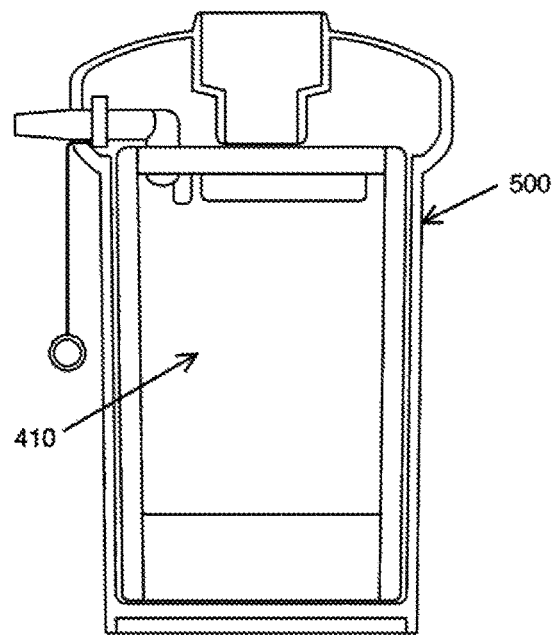
FIG. 5A is a sectional view illustrating a state where the disposable bag or the like according to the present invention is housed in a rigid container.
Figure 5B:
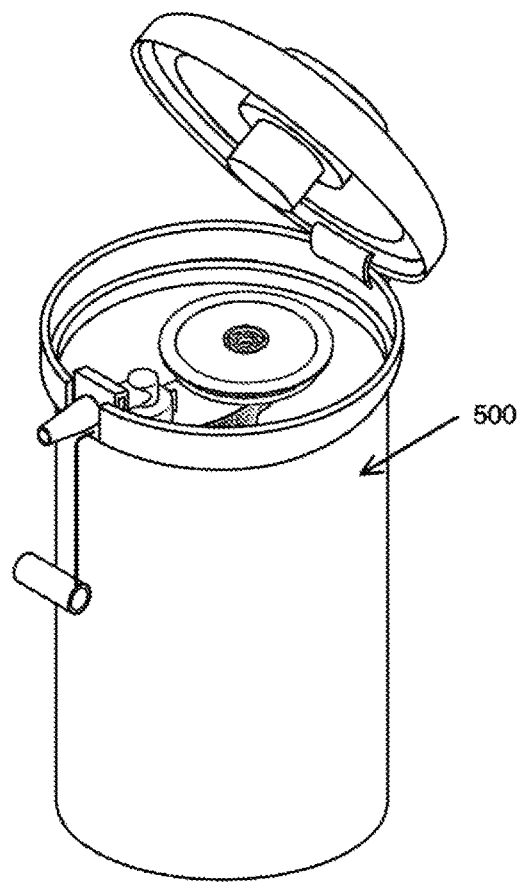
FIG. 5B is a perspective view illustrating a state where the lid of the rigid container housing the disposable bag or the like according to the present invention is open.

FIGS. 5A and 5B illustrate a state where a completed disposable bag is attached to a rigid container 500. Note that FIG. 5B illustrates an example where the air permeation component 300 mounted uses the circular complex molded body 310 illustrated in FIG. 3I.

Although descriptions have been given of the above embodiments, the present invention is not limited to them. It is apparent to those skilled in the art that the present invention can be changed and modified variously within the spirit of the present invention and the scope of claims attached hereto.

The invention claimed is:

1. A molded body filter that prevents passage of bacteria and viruses, the molded body filter being used for a medical aspirator system which includes
   a suction port to connect to a suction catheter to take in exhaled breath and secretions from a patient or a user,
   a rigid container main body and a lid portion thereof,
   a space which is provided in a void formed by the rigid container main body and the lid portion and retains only the secretions out of the exhaled breath and the secretions, and
   a discharge port provided to the rigid container main body to discharge an air and the exhaled breath other than the secretions retained in the space, the discharge being performed by an aspirator main body outside the rigid container main body,
   the molded body filter being configured so that the air and the exhaled breath other than the secretions always pass though the molded body filter before being sucked into the aspirator main body, and being placed in an airtight manner at a position downstream of a retention space for the secretions in a flow direction of the air and the exhaled breath, preventing passage of bacteria and viruses which may be contained in the exhaled breath and the secretions, wherein
   a base material of the molded body filter is formed of at least two materials which are a material including sodium carboxymethyl cellulose (CMC) in powder form and an electrically-charged nonwoven fabric, and
   the electrically-charged nonwoven fabric is placed downstream of the material including CMC in powder form in the flow direction.

2. The molded body filter that prevents passage of bacteria and viruses according to claim 1, comprising a flexible disposable bag or container as the retention space, the disposable bag or container being housed in the void formed by the rigid container main body and the lid portion, configured to retain only the secretions out of the exhaled breath and the secretions, and configured to be removed from the rigid container and disposed of after an amount of the secretions retained reaches a predetermined retention amount, wherein
   the disposable bag or container includes a molded body of an air permeation component having at least the suction port and an air release port communicating with the discharge port.

3. The molded body filter that prevents passage of bacteria and viruses according to claim 2, wherein
   the molded body filter includes
   a main body of a three-dimensionally shaped component having an internal cavity,
   a support portion provided to the three-dimensionally shaped component toward an inside of the disposable bag or container, the support portion being provided to join the filter base material,
   net-shaped ribs provided to the support portion to prevent a film-shaped filter base material from swelling in the flow direction,
   the filter base material joined onto the ribs in an airtight manner, and
   the air release port provided toward the discharge port of the rigid container.

4. The molded body filter that prevents passage of bacteria and viruses according to claim 3, wherein
   the three-dimensionally shaped component is shaped like a hollow cylinder or a cuboid.

5. The molded body filter that prevents passage of bacteria and viruses according to claim 3, wherein
   the support portion is a flat plate having a shape including a circle or rectangle, and
   an opening portion of the support portion is reinforced by the net-shaped ribs.

6. The molded body filter that prevents passage of bacteria and viruses according to claim 2, wherein
   the molded body filter is placed at the air permeation component in an airtight manner toward an inside of the disposable bag or container.

7. The molded body filter that prevents passage of bacteria and viruses according to claim 2, wherein
   the molded body filter is placed in contact with an outer side of the air permeation component, placed in contact with an inner side of the rigid container or the lid portion, or placed at some midpoint in a suction tube from the air release port to the rigid container or the lid portion.

8. The molded body filter that prevents passage of bacteria and viruses according to claim 1, wherein
   the molded body filter is removably placed at some midpoint in a connection hose connecting the aspirator main body and an air release portion of the rigid container.

9. The molded body filter that prevents passage of bacteria and viruses according to claim 1, wherein
   the filter base material of the molded body filter is configured such that
   the material including CMC in powder form is sandwiched and sealed by a hydrophobic porous film, and
   the electrically-charged nonwoven fabric is placed downstream in the flow of the exhaled breath.

10. The molded body filter that prevents passage of bacteria and viruses according to claim 9, wherein
    the filter base material of the molded body filter is configured such that
    the material including CMC in powder form is sandwiched and sealed between two hydrophobic porous films which are not electrically charged, and
    the electrically-charged nonwoven fabric is further placed downstream in the flow of the exhaled breath.

11. The molded body filter that prevents passage of bacteria and viruses according to claim 9, wherein
the filter base material of the molded body filter is configured such that
the material including CMC in powder form is sandwiched and sealed between a hydrophobic porous film and the electrically-charged nonwoven fabric, and
the electrically-charged nonwoven fabric is placed downstream in the flow of the exhaled breath.

12. The molded body filter that prevents passage of bacteria and viruses according to claim 9, wherein
the hydrophobic porous film has a maximum pore size ranging from 0.2 μm to 10 μm.

13. The molded body filter that prevents passage of bacteria and viruses according to claim 12, wherein
the hydrophobic porous film has a maximum pore size ranging from 1 μm to 5 μm.

14. The molded body filter that prevents passage of bacteria and viruses according to claim 1, wherein
the electrically-charged nonwoven fabric is made of a material containing a polypropylene resin (PP) or a nylon 66 resin.

15. The molded body filter that prevents passage of bacteria and viruses according to claim 1, wherein,
a charge amount of the electrically-charged nonwoven fabric is $2.0 \times 10^{-10}$ coulombs/cm$^2$ or greater in terms of a surface charge density.

* * * * *